US006964766B1

(12) United States Patent
Verheijden et al.

(10) Patent No.: US 6,964,766 B1
(45) Date of Patent: Nov. 15, 2005

(54) PEPTIDES FOR USE IN IMMUNOTHERAPY OF AUTOIMMUNE DISEASES

(75) Inventors: Gijsbertus Franciscus Maria Verheijden, Heischouw (NL); Anna Maria Helena Boots, Verlengde Torenstraat (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/744,170
(22) PCT Filed: Jul. 16, 1999
(86) PCT No.: PCT/EP99/05050
§ 371 (c)(1),
(2), (4) Date: Apr. 5, 2001
(87) PCT Pub. No.: WO00/05254
PCT Pub. Date: Feb. 3, 2000

(30) Foreign Application Priority Data

Jul. 23, 1998 (EP) .......................... 98202470

(51) Int. Cl.$^7$ .............................. A61K 39/00
(52) U.S. Cl. ................. 424/184.1; 530/328; 530/327; 514/14; 514/15; 435/7.1; 435/29

(58) Field of Search ................ 530/300; 514/12–15; 435/7.8; 424/185.1

(56) References Cited

FOREIGN PATENT DOCUMENTS

| EP | 0 805 206 | 11/1997 |
| WO | WO 96 13517 | 5/1996 |
| WO | WO 97 40068 | 10/1997 |
| WO | WO 98 06859 | 2/1998 |

OTHER PUBLICATIONS

Hu et al. JBC vol 271, pp. 19415–19420, 1996.*
Wendling et al. J of Immunology. vol: 164: 2711–2717, 2000.*

* cited by examiner

Primary Examiner—Patrick J. Nolan
(74) Attorney, Agent, or Firm—William P. Ramey; William M. Blackstone (57) ABSTRACT

The invention relates to the use of novel peptides in a peptide induced tolerance therapy to prevent autoimmune disorders and in particular their use in treatment of chronic destruction of articular cartilage. The invention furtermore embraces pharmaceutical compositions comprising said peptides and a diagnostic method for the detection of autoreactive T cells in a test sample.

9 Claims, 6 Drawing Sheets

SEQUENCE LISTING

```
<160> NUMBER OF SEQ ID NOS: 5

<210> SEQ ID NO 1
<211> LENGTH: 9
<212> TYPE: PRT
<213> ORGANISM: Homo sapiens

<400> SEQUENCE: 1

Phe Thr Leu Ala Ser Ala Glu Thr Thr
 1               5

<210> SEQ ID NO 2
<211> LENGTH: 13
<212> TYPE: PRT
<213> ORGANISM: Homo sapiens

<400> SEQUENCE: 2

His Ser Phe Thr Leu Ala Ser Ala Glu Thr Thr Val Gly
 1               5                   10

<210> SEQ ID NO 3
<211> LENGTH: 13
<212> TYPE: PRT
<213> ORGANISM: Homo sapiens
```

```
<400> SEQUENCE: 3

Arg Ser Phe Thr Leu Ala Ser Ser Glu Thr Gly Val Gly
 1               5                  10

<210> SEQ ID NO 4
<211> LENGTH: 14
<212> TYPE: PRT
<213> ORGANISM: Homo sapiens

<400> SEQUENCE: 4

Arg Ser Phe Thr Leu Ala Ser Ser Asp Thr Arg Val Gly
 1               5                  10

<210> SEQ ID NO 5
<211> LENGTH: 13
<212> TYPE: PRT
<213> ORGANISM: Homo sapiens

<400> SEQUENCE: 5

Pro Lys Phe Val Lys Gln Asn Thr Leu Lys Leu Ala Thr
 1               5                  10
```

PEPTIDES FOR USE IN IMMUNOTHERAPY OF AUTOIMMUNE DISEASES

This application is a 35 U.S.C. 371 National Phase application of PCT/EP99/05050 filed Jul. 16, 1999, which is based for priority on European Application EP 98202470.5 filed Jul. 23, 1998.

The invention relates to novel peptides, their use in treatment of chronic destruction of articular cartilage in autoimmune diseases, pharmaceutical compositions comprising said peptide, and a diagnostic method for the detection of autoreactive T cells in a test sample.

The immune system is established on a principle of discrimination between foreign antigens (non-self antigens) and autoantigens (self antigens, derived from the individuals own body) achieved by a build-in tolerance against the autoantigens.

The immune system protects individuals against foreign antigens and responds to exposure to a foreign antigen by activating specific cells such as T- and B lymphocytes and producing soluble factors like interleukins, antibodies and complement factors. The antigen to which the immune system responds is degraded by the antigen presenting cells (APCs) and a fragment of the antigen is expressed on the cell surface associated with a major histocompatibility complex (MHC) class II glycoprotein. The MHC-glycoprotein-antigen-fragment complex is presented to a T cell which by virtue of its T cell receptor recognizes the antigen fragment conjointly with the MHC class II protein to which it is bound. The T cell becomes activated, i.e. proliferates and/or produces interleukins, resulting in the expansion of the activated lymphocytes directed to the antigen under attack (Grey et al., Sci. Am., 261:38–46, 1989).

Self antigens are also continuously processed and presented as antigen fragments by the MHC glycoproteins to T cells (Jardetsky et al., Nature 353:326–329, 1991). Self recognition thus is intrinsic to the immune system. Under normal circumstances the immune system is tolerant to self antigens and activation of the immune response by these self antigens is avoided.

When tolerance to self antigens is lost, the immune system may become activated against one or more self antigens, resulting in the activation of autoreactive T cells and the production of autoantibodies. This phenomenon is referred to as autoimmunity. As the immune response in general is destructive, i.e. meant to destroy the invasive foreign antigen, autoimmune responses can cause destruction of the body's own tissue.

The contribution of T cells to autoimmune diseases has been established in several studies. In mice, experimental autoimmune encephalomyelitis (EAE) is mediated by a highly restricted group of T cells, linked by their specificity for a single epitope of myelin basic protein (MBP) complexed to an MHC class II molecule. In the Lewis rat, a species with high susceptibility to various autoimmune diseases, disease has been shown to be mediated by T cells. In humans autoimmune diseases are also thought to be associated with the development of auto-aggressive T cells.

A destructive autoimmune response has been implicated in various diseases such as rheumatoid arthritis (RA), in which the integrity of articular cartilage is destroyed by a chronic inflammatory process resulting from the presence of large numbers of activated lymphocytes and MHC class II expressing cells. The mere presence of cartilage appears necessary for sustaining the local inflammatory response: it has been suggested that cartilage degradation is associated with the activity of cartilage-responsive autoreactive T cells in RA (Sigall et al., Clin. Exp. Rheumat. 6:59, 1988; Glant et al., Biochem. Soc. Trans. 18:796, 1990; Burmester et al., Rheumatoid artritis Smolen, Kalden, Maini (Eds) Springer-Verlag Berlin Heidelberg, 1992). Furthermore, removal of cartilage from RA patients by surgery was shown to reduce the inflammatory process (R. S. Laskin, J. Bone Joint Surgery (Am) 72:529, 1990). The cartilage proteins are therefore considered to be target autoantigens which are competent of stimulating T cells. Activation of these autoreactive T cells leads to development of autoimmune disease. However, the identification of the autoantigenic components that play a role in the onset of rheumatoid arthritis has so far remained elusive.

The inflammatory response resulting in the destruction of the cartilage can be treated by several drugs, such as for example steroid drugs. However, these drugs are often immunosuppressive drugs that are nonspecific and have toxic side effects. The disadvantages of nonspecific immunosuppression makes this a highly unfavourable therapy.

The antigen-specific, nontoxic immunosuppression therapy provides a very attractive alternative for the non-specific immunosuppression. This antigen-specific therapy involves the treatment of patients with the target autoantigen or with synthetic T cell-reactive peptides derived from the autoantigen. These synthetic peptides correspond to T cell epitopes of the autoantigen and can be used to induce specific T cell tolerance both to themselves and to the autoantigen. Although it seems paradoxical to desensitize the immune system with the very same antigen responsible for activating the immune system, the controlled adminstration of the target (auto)antigen can be very effective in desensitization of the immune system. Desensitization or immunological tolerance of the immune system is based on the long-observed phenomenon that animals which have been fed or have inhaled an antigen or epitope are less capable of developing a systemic immune response towards said antigen or epitope when said antigen or epitope is introduced via a systemic route.

The human cartilage glycoprotein-39 (HC gp-39) was previously identified as a target autoantigen in rheumatoid arthritis (RA) (Verheijden et al., Arthitis Rheum. 40:1115–1125, 1997). The strategy followed for identification of relevant auto-epitopes within HC gp-39 was based on the assumption that the DR4 or DR1 molecules predispose to RA (Gao et al., Arthitis Rheum. 33:939–946, 1990; Nelson et al., Rheumatoid Arthritis, In Proceedings of the Eleventh International Histocompatibility Workshop and Conference. Vol 1, Tsuji et al Ed, Oxford University Press, 1991) at two levels, firstly, by shaping the T cell repertoire and secondly, by determinant selection. The shared epitope found among the RA-associated DR molecules might be involved in selection of similar sets of peptides for presentation to T cells (Gregerson et al., Arthitis Rheum. 30:1205–1213, 1987). Putative binding sequences within the primary structure of HC gp-39 were identified by use of a DR4 (B1*0401) peptide binding motif (Verheijden et al., Arthitis Rheum. 40:1115–1125, 1997). HC gp-39, a protein of 362 amino acids, excluding the signal sequence (Hakala et al., J. Biol. Chem. 268:25803–25810, 1993), contains six regions accommodating this motif. Four peptides thus selected were synthesized and tested for binding the RA-associated DR1 and DR4 (B1*0401 and 0404) variants. All motif-based peptides, spanning residues 103–116, 259–275, 263–275 and 326–338 of HC gp-39, were found to bind with high relative affinity to DRB1*0401 molecules. The recognition of these peptides by peripheral blood T cells from RA patients and healthy donors was subsequently examined. All motif-based peptides were readily recognized in RA patients, thereby suggesting a high frequency of HC gp-39-specific T cells in RA. The response to 263–275 was most prominent; 8 out of 18 RA patients responded to this peptide (Verheijden et al., Arthitis Rheum. 40:1115–1125, 1997). Thus, HC gp-39 is a target for immune recognition in the joint.

The significance of this protein for arthritic disease was further demonstrated by its arthritogenicity in Balb/c mice. A single injection in the chest region with µg amounts of protein mixed in IFA, induced a chronic joint inflammation reminiscent of RA (Verheijden et al., Arthitis Rheum 40:1115–1125, 1997).

Recently, a novel human chondrocyte protein, YKL-39, was isolated and described (Hu et al., J.Biol.Chem. 271: 19415–19420, 1996). The protein shares significant sequence identity with HC gp-39 (YKL-40). Another homologue of HC gp-39 is secreted by human macrophages and is termed chitotriosidase (Boot et al., J.Biol.Chem. 270: 26252–26256, 1995). The sequences corresponding to the HC gp-39 (263–275) peptide RSFTLASSETGVG (SEQ ID NO:3) are identified as HSFTLASAETTVG (SEQ ID NO:2) within the YKL-39 protein (266–278) and as RSFTLASSS-DTRVG (SEQ ID NO:4) within macrophage chitotriosidase (269–282) respectively (Table 1).

The chitotriosidase peptide Chi (269–282) contains the DRB1*0401, peptide binding motif which was previously used for selection of T-cell epitopes within proteins. In contrast, the YKL-39 (266–278) peptide does not contain this 0401 motif.

It will be clear that tolerization of HC gp-39 (263–275)-reactive T-cells may be of benefit to RA patients. Likewise, mimicry epitopes of HC gp39 (263–275) may have a similar function and may be used to induce tolerance. Preferably such mimicry epitopes will have at least the same tolerizing capacity.

To effectively use tolerance induction therapy to treat T cell mediated cartilage destruction, there is a great need to identify T cell-reactive peptides which can desensitize patients against the autoantigen that is activating the T cells responsible for the inflammatory process.

Although the YKL-39 peptide does not contain the 0401 motif, it was surprisingly found that the YKL-39 (266–278) epitope is a mimicry epitope of HC gp-39 (263–275).

This epitope therefore is useful for tolerization of autoreactive T-cells with reactivity to HC gp-39 (263–275), YKL-39 (266–278) or their mimicry epitopes in rheumatoid arthritis patients.

It is an object of the invention to provide peptides which are able to induce systemic immunological tolerance, more in particular specific T cell tolerance, preferably to the responsible cartilage antigen in patients suffering from T cell-mediated cartilage destruction. The peptides of the present invention are characterized in that they comprise one or more of the amino acid sequences FTLASAETT (SEQ ID NO: 1). More specifically, a peptide according to the invention comprises HSFTLASAETTVG (SEQ ID NO: 2).

Also within the scope of the invention are multimers of the peptides according to the invention such as for example a dimer or trimer of the peptides according to the invention. A multimer according to the invention can either be a homomer, consisting of a multitude of the same peptide, or a heteromer consisting of different peptides.

The characteristic amino acid sequences of the peptides according to the invention can be flanked by random amino acid sequences. Preferred are flanking sequences, that have a stabilizing effect on the peptides, thus increasing their biological availability.

Human Cartilage glycoprotein 39 is a target autoantigen in RA patients which activates specific T cells, thus causing or mediating the inflammatory process. HC gp-39 derived peptides were predominantly recognized by autoreactive T cells from RA patients but rarely by T cells from healthy donors, thus indicating that HC gp-39 is an autoantigen in RA. The arthritogenic nature of HC gp-39 was further substantiated in the Balb/c mouse. A single, subcutaneous injection of said protein in Balb/c mice was able to initiate arthritic signs in the animals. The course of the HC gp-39-induced disease was characterized by relapses occuring periodically in fore paws and/or hind paws and gradually developed from a mild arthritis into a more severe form. Also, a symmetrical distribution of afflicted joints was observed which is, together with the observation of recurrent relapses, reminiscent of disease progression in arthritis, especially RA.

It was surprisingly found that the YKL-39 266–278 peptide was effective as a tolerogen. It will be clear to those skilled in the art that the peptides may be extended at either side of the peptide or at both sides and still exert the same immunological function. The extended part may be an amino acid sequence similar to the natural sequence of the protein YKL-39.

The peptides according to the invention can be prepared by well known organic chemical methods for peptide synthesis such as, for example, solid-phase peptide synthesis described for instance in J. Amer. Chem. Soc. 85:2149 (1963) and Int J. Peptide Protein Res. 35:161–214 (1990). The peptides according to the invention can also be prepared by recombinant DNA techniques. A nucleic acid sequence coding for a peptide according to the invention or a multimer of said peptides is inserted into an expression vector. Suitable expression vectors comprise the necessary control regions for replication and expression. The expression vector can be brought to expression in a host cell. Suitable host cells are, for instance, bacteria, yeast cells and mammalian cells. Such techniques are well known in the art, see for instance Sambrooke et al, Molecular Cloning:a Laboratory Manual, Cold Spring Harbor laboratory Press, Cold Spring Harbor, 1989.

The peptides may be stabilised by C- and/or N- terminal modifications, which will decrease exopeptidase catalysed hydrolysis. The modifications may include: C-terminal acylation, (e.g acetylation =Ac-peptide), N-terminal amide introduction, (e.g. peptide-$NH_2$) combinations of acylation and amide introduction (e.g. Ac-peptide-$NH_2$) and introduction of D-amino acids instead of L-amino acids (Powell et al., J. Pharm Sci., 8:731–735, 1992).

Other modifications are focussed on the prevention of hydrolysis by endopeptidases. Examples of these modifications are: introduction of D-amino acids instead of L-amino acids, modified amino acids, cyclisation within the peptide, introduction of modified peptide bonds, e.g. reduced peptide bonds $\psi[CH_2NH]$ and e.g. peptoids (N-alkylated glycine derivatives) (Adang et al, Recl. Trav. Chim. Pays-Bas, 113:63–78, 1994 and Simon et al, Proc. Natl. Acad. Sci. USA, 89:9367–9371, 1992).

The peptides according to the invention are T-cell epitopes, which are recognized by and are able to stimulate autoreactive T-cells. These autoreactive T cells may be found e.g. in the blood of patients suffering from autoimmune diseases.

Thus, according to the invention the peptides, said peptides resembling the MHC Class II restricted T-cell epitopes present on the target autoantigen comprising the peptide of SEQ ID NO:1 or SEQ ID NO:2, are very suitable for use in a therapy to induce specific T-cell tolerance to said autoantigen in mammals, more specifically humans, suffering from T-cell mediated cartilage destruction, such as for example arthritis, more specifically rheumatoid arhritis. Optionally such a treatment can be combined with the the administration of other medicaments such as DMARDs (Disease Modifying Anti-Rheumatic Drugs e.g. sulfasalazine, antimalarials (chloroquine, hydroxychloroquine) injectable or oral gold, methotrexate, D-penicillamine, azathioprine, cyclosporine, mycophenolate), NSAIDs (non steroidal anti inflammatory drugs), corticosteroids or other drugs knowns to influence the course of the disease in autoimmune patients.

The peptides according to the invention can also be used to modulate lymphocytes that are reactive to antigens other than said autoantigen but are present in the same tissue as the autoantigen i.e. proteins or parts thereof comprising the peptide according to SEQ ID NO:1 or SEQ ID NO:2. By the induction of antigen-specific T-cell tolerance, autoimmnune disorders can be treated by bystander suppression. More in general, the cells to be modulated are hematopoietic cells. In general, in order to fuction as a tolerogen the peptide must fulfill at least two conditions i.e. it must possess an immune modulating capacity and it must be expressed locally usually as part of a larger protein.

Thus, the present invention provides a method to treat patients suffering from inflammatory autoimmune diseases, by administration of a pharmaceutical preparation comprising the peptide according to the invention. Such patients may suffer from diseases like Graves' diseases, juvenile arthritis, primary glomerulonephritis, osteoarthritis, Sjögren's syndrome, myasthenia gravis, rheumatoid arthritis, Addison's disease, primary biliary sclerosis, uveitis, systemic lupus erythematosis, inflammatory bowel disease, multiple sclerosis or diabetes. The peptides according to the present invention therefore can be used in the preparation of a pharmaceutical to induce tolerance in patients suffering from these diseases.

Treatment of autoimmune disorders with the peptides according to the invention makes use of the fact that bystander suppression is induced to unrelated but co-localized antigens. The regulatory cells secrete in an antigen specific fashion pleiotropic proteins such as cytokines which may downmodulate the immune response.

According to the invention, patients suffering from T-cell mediated destruction of the articular cartilage can be treated with a therapeutical composition comprising one or more peptides according to the invention and a pharmaceutical acceptable carrier. Administration of the pharmaceutical composition according to the invention will induce systemic immunological tolerance, in particular tolerance of the specific autoreactive T cells of these patients, to the autoantigenic proteins in the articular cartilage under attack and other self antigens which display the identified MHC Class II binding T cell epitopes characterized or mimicked by the amino acid sequences of one or more of the peptides according to the invention. The induced tolerance thus will lead to a reduction of the local inflammatory response in the articular cartilage under attack.

Very suitable peptides to be used in a pharmaceutical composition according to the invention are the peptides comprising the YKL-39 (268–276) or the YKL-39 (266–278) peptide flanked by sequences up to a total length of 55 amino acids. More preferably the peptides have a length of 25 amino acids. Even more preferably the amino acid sequence of the peptides is FTLASAETT (SEQ ID NO: 1) or HSFTLASAETTVG (SEQ ID NO: 2).

The peptides according to the invention have the advantage that they have a specific effect on the autoreactive T cells thus leaving the other components of the immune system intact as compared to the nonspecific suppressive effect of immunosuppressive drugs. Treatment with the peptides according to the invention will be safe and no toxic side effects will occur.

Systemic immunological tolerance can be attained by administering high or low doses of peptides according to the invention. The amount of peptide will depend on the route of administration, the time of administration, the age of the patient as well as general health conditions and diet.

In general, a dosage of 0.01 to 10000 µg of peptide per kg body weight; preferably 0.05 to 500 µg, more preferably 0.1 to 100 µg of peptide can be used.

Pharmaceutical acceptable carriers are well known to those skilled in the art and include, for example, sterile saline, lactose, sucrose, calcium phosphate, gelatin, dextrin, agar, pectin, peanut oil, olive oil, sesame oil and water. Other carriers may be, for example MHC class II molecules, if desired embedded in liposomes.

In addition the pharmaceutical composition according to the invention may comprise one or more adjuvants. Suitable adjuvants include, amongst others, aluminum hydroxide, aluminum phosphate, amphigen, tocophenols, monophosphenyl lipid A, muramyl dipeptide and saponins such as Quill A. Preferably, the adjuvants to be used in the tolerance therapy according to the invention are mucosal adjuvants such as the cholera toxine B-subunit or carbomers, which bind to the mucosal epithelium. The amount of adjuvant depends on the nature of the adjuvant itself.

Furthermore the pharmaceutical composition according to the invention may comprise one or more stabilizers such as, for example, carbohydrates including sorbitol, mannitol, starch, sucrosedextrin and glucose, proteins such as albumin or casein, and buffers like alkaline phosphates.

Suitable administration routes are e.g. intramuscular injections, subcutaneous injections, intravenous injections or intraperitoneal injections, oral administration and nasal administration such as sprays.

It is another object of the invention to provide a method for detecting autoreactive T cells involved in the destruction of articular cartilage and test kits to be used in said method. Thus, the peptides according to the invention are also very suitable for use in a diagnostic method to detect the presence of activated autoreactive T cells involved in the chronic inflammation and destruction of the articular cartilage.

The diagnostic method according to the invention comprises the following steps:

a) isolation of the peripheral blood mononuclear cells (PBMC) from a blood sample of an individual, b) culture said PBMC under suitable conditions, c) incubation of said PBMC culture in the presence of one or more peptides according to the invention, and d) detection of a response of T cells, for example a proliferative response, indicating the presence of activated autoreactive T cells in the individual.

The detection of a proliferative response of T cells can be detected by, for example, the incorporation of $^3$H-thymidine.

Also within the scope of the invention are test kits which comprise one or more peptides according to the invention. These test kits are suitable for use in a diagnostic method according to the invention.

The following examples are illustrative for the invention and should in no way be interpreted as limiting the scope of the invention.

BRIEF DESCRIPTION OF THE FIGURES

FIG. 1

(CVR0271B-HC gp39 (263–275), KV0432B=YKL-39 (266–278), CC0332B=Chi (269–282) KV0431A=YKL-39 (262–274). HCDA.8B12.1D8, 14G11.1H7and 20H5.4F6.2F6 are HLA-DRB1*0401- restricted hybridomas specific for HC gp-39 (263–275). Activation of T-cell hybridomas is expressed as IL-2 production.

FIG. 2

Balb/c mice were tolerized by intranasal application of 50, 10 or 2 micrograms of HC gp-39 (263–275), SEQ ID NO: 3, (FIG. 2b) or YKL-39 (266–278) (FIG. 2c) followed by immunization with HC gp-39 (263–275). Mice that were pretreated with saline or that were left untreated were included as controls (FIG. 2a).

EXAMPLES

Example 1 Alignment of Sequences

The human chondrocyte protein, YKL-39 shares significant sequence identity with HC gp-39 (YKL-40). Another homologue of HC gp-39 is secreted by human macrophages and is termed chitotriosidase (Boot et al., 1995). The sequences corresponding to RSFTLASSETGVG (HC gp-39 (263–275), SEQ ID NO: 3) were identified as HSFTLASA-ETTVG (SEQ ID NO: 2) within the YKL-39 protein (266–278) and as RSFTLASSSDTRVG (SEQ ID NO: 4) within macrophage chitotriosidase (269–282) respectively (Table 1). Chi (269–282) contains the HLA-DRB1*0401 peptide binding motif which was previously used for selection of T-cell epitopes within proteins. In contrast, the YKL-39 (266–278) peptide does not contain this motif. All peptides were synthesized.

TABLE 1

Alignment of the HC gp-39 (263-278) sequence with the corresponding region in YKL-39 and macrophage Chitotriosidase.

| | |
|---|---|
| HCgp-39 263-275 | R S F T L A S S - E T G V G (SEQ ID NO: 3) |
| YKL-39 266-278 | H S F T L A S A - E T T V G (SEQ ID NO: 2) |
| Chi (269-282) | R S F T L A S S S D T R V G (SEQ ID NO: 4) |

Example 2 Binding of Peptides to HLA-DRB1*0401

The peptides from example 1 were tested for binding the DRB1*0401-encoded molecules. HLA-DR4 (DRB1*0401) molecules were purified from the homozygous EBV-transformed human B lymphoblastoid cell lines Huly138IC2 and the competition peptide HLA-DR binding assay was performed basically as described by Verheijden et al., 1997. The affinity of a given peptide for binding DRB1*0401-encoded molecules was related to competition with a marker peptide. This relative binding affinity was defined as the peptide concentration at which the signal was reduced to 50% (IC50). The HA-F peptide is a positive control (Hemagglutinin 307–319; PKFVKQNTLKLAT; at position 309 Y is substituted by F; SEQ ID NO: 5). The peptide is known to have a high affinity for DRB1*0401 molecules.

As expected, the Chi (269–282) peptide was found to bind with high affinity to DRB1*0401 (see table 2). The YKL-39 (266–278) peptide, which does not accommodate the effective DRB1*0401 peptide binding motif, bound with very high affinity to DR4 (B1*0401).

TABLE 2

Peptide binding to HLA-DRB1*0401-encoded molecules

| | | IC50 values | | |
|---|---|---|---|---|
| peptide | batch | Exp.A | Exp.B | Exp.C |
| YKL39(262-274) | KV0431A | 0.006 | 0.005 | ND |
| YKL39(266-278) | KV432B | 0.035 | 0.032 | 0.12 |
| HCgp39(263-275) | CVR271B | ND | 0.008 | 0.038 |
| Chi(269-282) | CC0332B | 0.053 | 0.11 | 0.16 |
| HA-F | AE0690A | 0.20 | 0.14 | 0.20 |

ND = not determined

Example 3 Stimulation T-cell Hybridomas

Hybridomas specific for HC gp-39 (263–275) were tested for recognition of the corresponding sequences.

To test the cross reactivity of the 3 different, HC gp39-specific hybridoma cell lines with the YKL-39 or the chitotriosidase peptide, $5 \times 10^4$ hybridoma cells and $2 \times 10^5$ irradiated (12000 RAD), EBV-transformed B cells carrying the DRB1*0401 specificity were incubated in 150 μl volumes in wells of a round-bottomed microtiter plate. Peptide antigen (HC gp-39 (263–275), YKL-39 (266–278), chitotriosidase (269–282) or a control peptide) was added in 50 μl volumes to duplicate wells. Forty-eight hr later 100 μl of the culture supernatant was assayed for IL-2 production using a sandwich ELISA with Pharmingen antibodies specific for mouse IL-2.

Figure 1A:
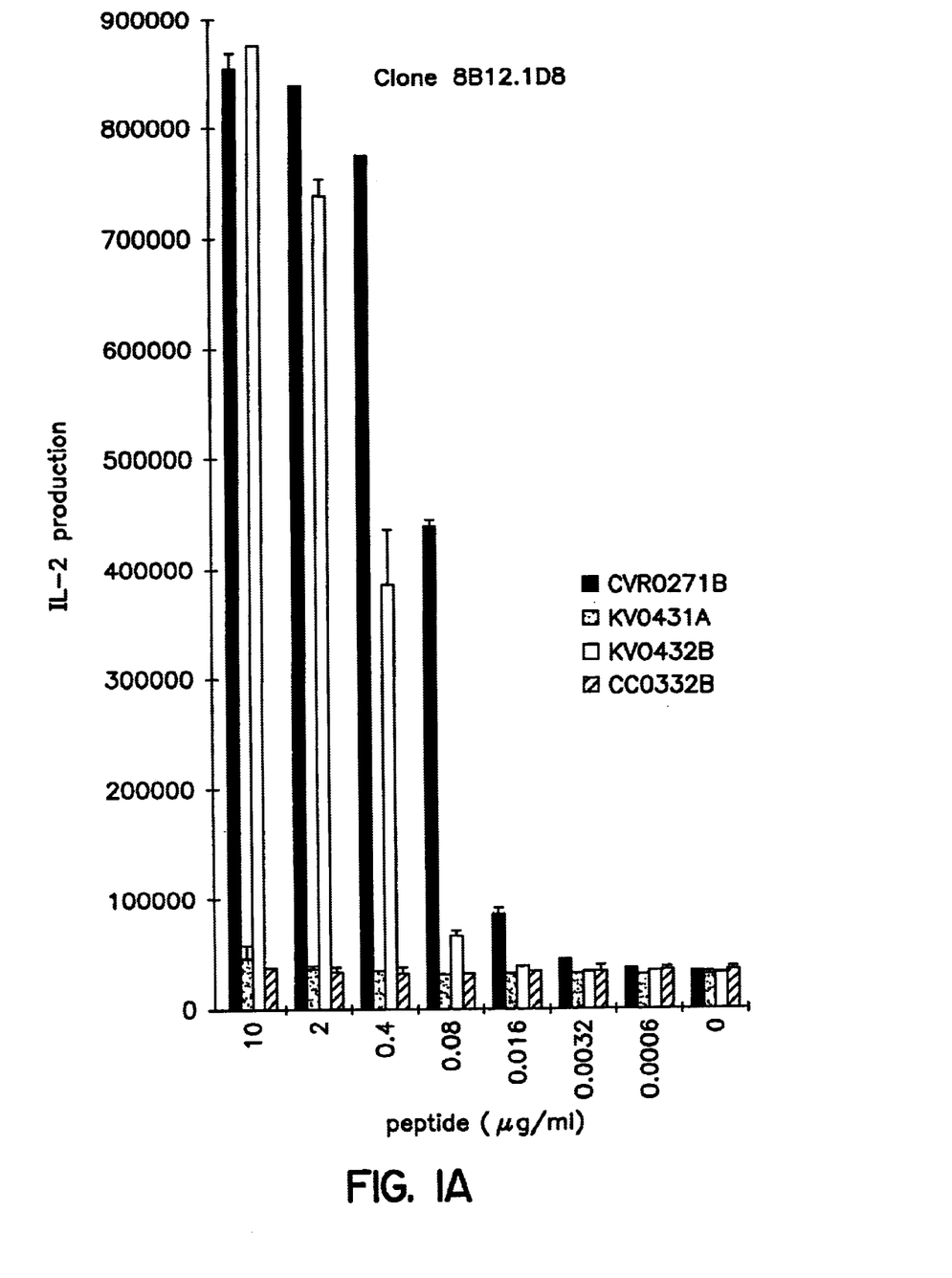
FIG. 1a, b, c. Cross reactivity of three, different, HC gp-39-specific hybridomas (8B12, 14G11, 20H5with YKL-39 (266–278).
Figure 1B:
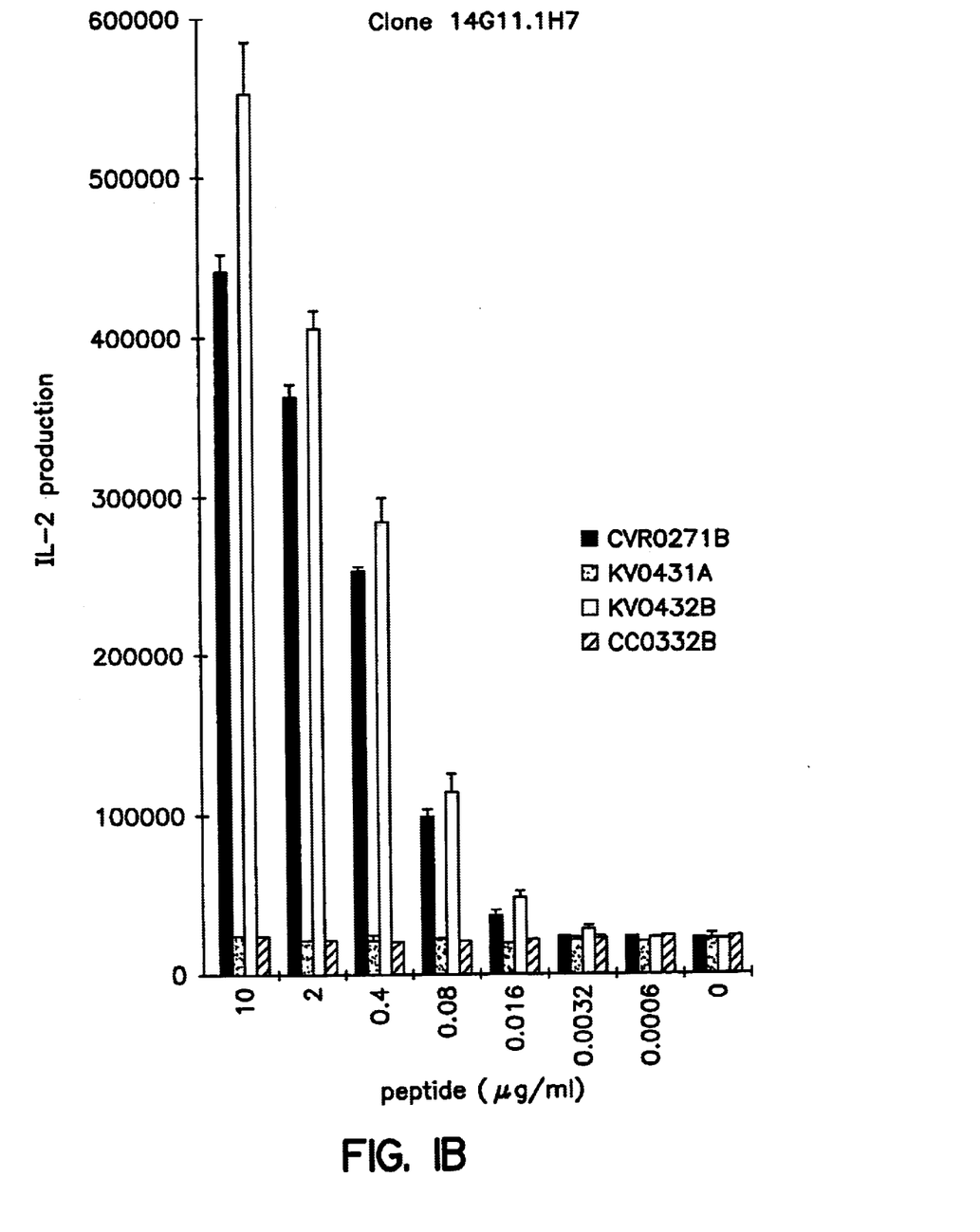
Figure 1C:
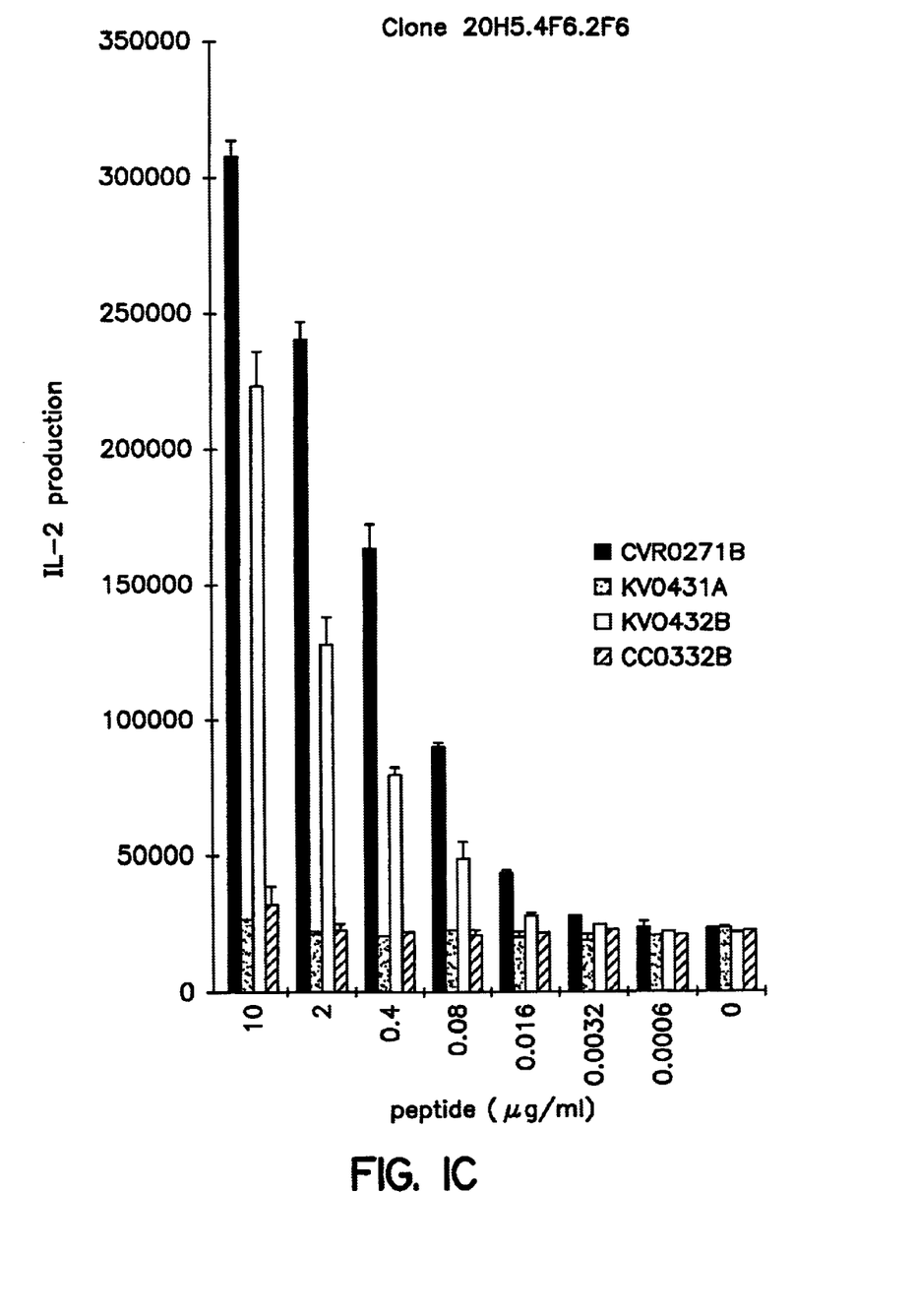

It was found that the synthetic peptide YKL-39 (266–278) generated a response similar to HC gp-39 (263–275) whereas the Chi (269–282) did not generate a response. The data suggest that the three different TCRs utilized by three different hybridomas do not discriminate between HC gp-39 (263–275) or YKL-39 (268–278) when presented by DRB1*0401-encoded molecules (FIGS. 1a, b, c) but do discriminate between HC gp-39 (263–275) and Chi (269–282). The data indicate that YKL-39 (266–278) is a mimicry epitope of HC gp-39 (263–275). (FIGS. 1a,b,c).

Example 4 Recognition of YKL-39 (266–278) by PBMC

Peripheral blood mononuclear cells (PBMC) were isolated from heparinized peripheral blood by standard centrifugation on Ficoll-Paque (Pharmacia, Uppsala, Sweden). Cells were suspended in wells of a 24 well plate in a concentration of $5 \times 10^5$ cells per ml. Cells were incubated in medium alone or in the presence of 10 or 50 μg/ml peptide antigen (YKL-39 (266–278)). Cultures were incubated for 6 days at 37° C. in a humidified atmosphere of 5% CO2. Cells were then suspended and 100 or 150 μl volumes of medium was distributed in 4-fold in wells of a 96-well roundbottomed plate. Cells were then pulsed with 0.5 μCi ($1.85 \times 10^4$ Bq) [3H]thymidine ([3H]TdR) and 18 hr later incorporated radioactivity was measured. Results as shown in table 3 are expressed as stimulation indices (SI) (antigen-specific counts/background counts).

From Table 3a it can be concluded that the YKL-39 (266–278) epitope is readily recognized in RA patients. Table 3b indicates that recognition of YKL,39 (266–278)) by PBMC coincides with recognition of HC gp-39

(263–275) and HC gp-39 and furthermore that recognition of YKL-39 (266–278) is generally more pronounced than recognition of HC gp-39 (263–275).

TABLE 3a

Recognition of the YKL-39 (266-278) epitope by PBMC from RA patients.

| Donor | typing | SI 10 µg/ml | SI 50 µg/ml |
|---|---|---|---|
| 242-0.2 | NR | 0404/15 | 3 | <2 |
| 337-0.2 | R | 0401/02 | 19 | 58 |
| 338-0.1 | NR | 03/14 | <2 | <2 |
| 454-0 | R | 0401/ | 9 | 9 |
| 456-0 | R | ND | 15 | 4 |
| 457-0 | NR | ND | <2 | <2 |
| 458-0 | R | ND | 4 | 27 |
| 459-0 | R | ND | <2 | 25 |
| 460-0 | NR | ND | 3 | <2 |

SI = antigen-specific counts/background counts. SI ≧ 5 are regarded positive R = responder, NR = non-responder TABLE 3b Recognition of YKL-39 (266-278) coincides with recognition of HC gp-39(263-275) and HC gp-39 protein.

| | | YKL-39(266-278) | | HC gp-39(263-275) | | HC gp-39 | |
|---|---|---|---|---|---|---|---|
| Donor | R/N µg/ml | SI 10 | SI 50 | SI 10 | SI 50 | SI 10 | SI 50 |
| 169 | R | 27 | 32 | 10 | 27 | 24 | 44 |
| 455 | R | 20 | 35 | 1 | 15 | 45 | 95 |
| 447 | NR | 1 | 2 | 1 | 1 | 1 | 1 |
| 327 | R | 6 | 5 | 3 | 5 | 12 | 19 |

SI = antigen-specific counts/background counts. SI ≧ 5 are regarded positive. R = responder, NR = non-responder. NT = not tested. Donor 447 responds to Tetanus toxoid and Candida Albicans.

Example 5 Tolerance Induction

Figure 2A:
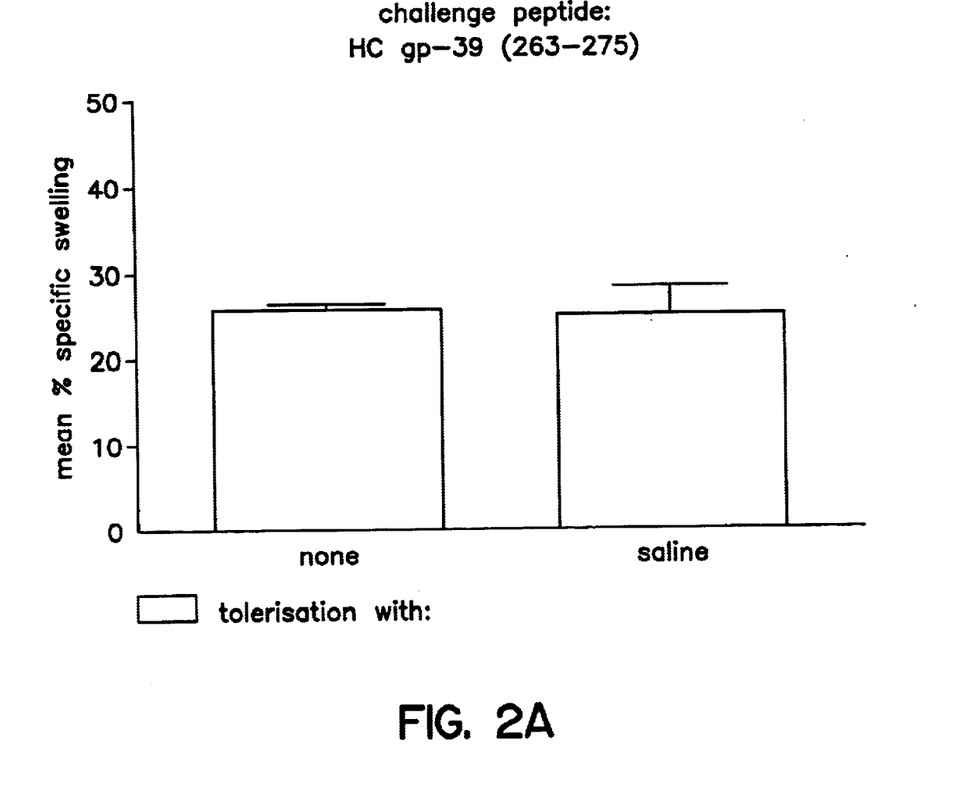
FIG. 2a, 2b, 2c In vivo tolerization with HC gp-39 (263–275) or YKL-39 (266–268)
Figure 2B:
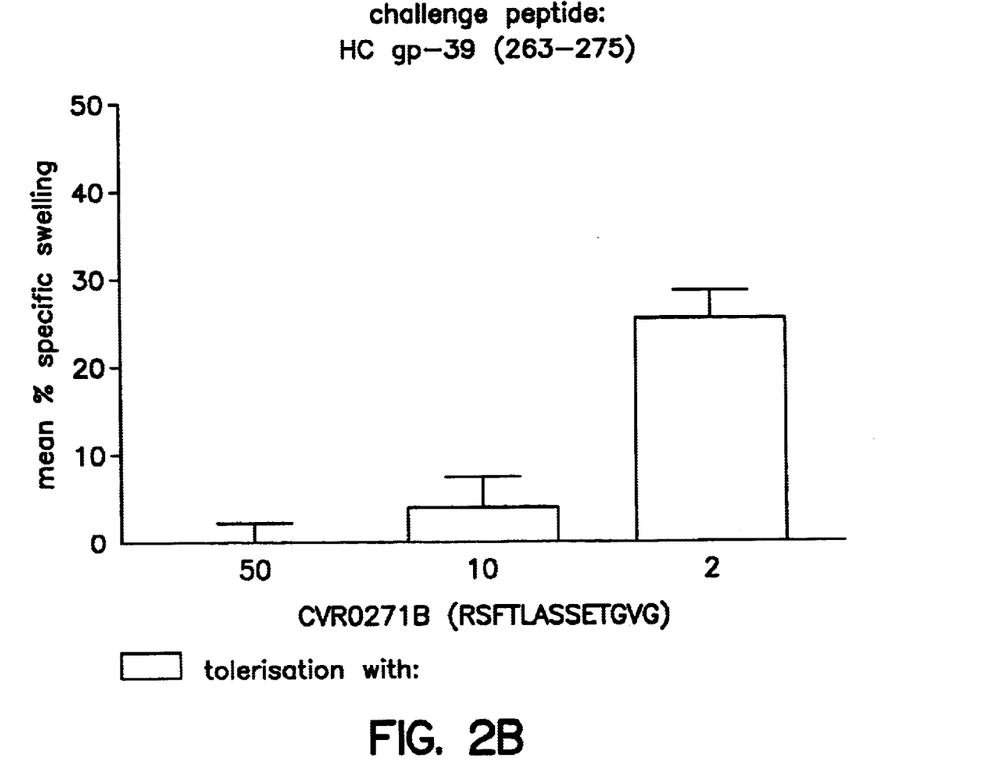
Figure 2C:
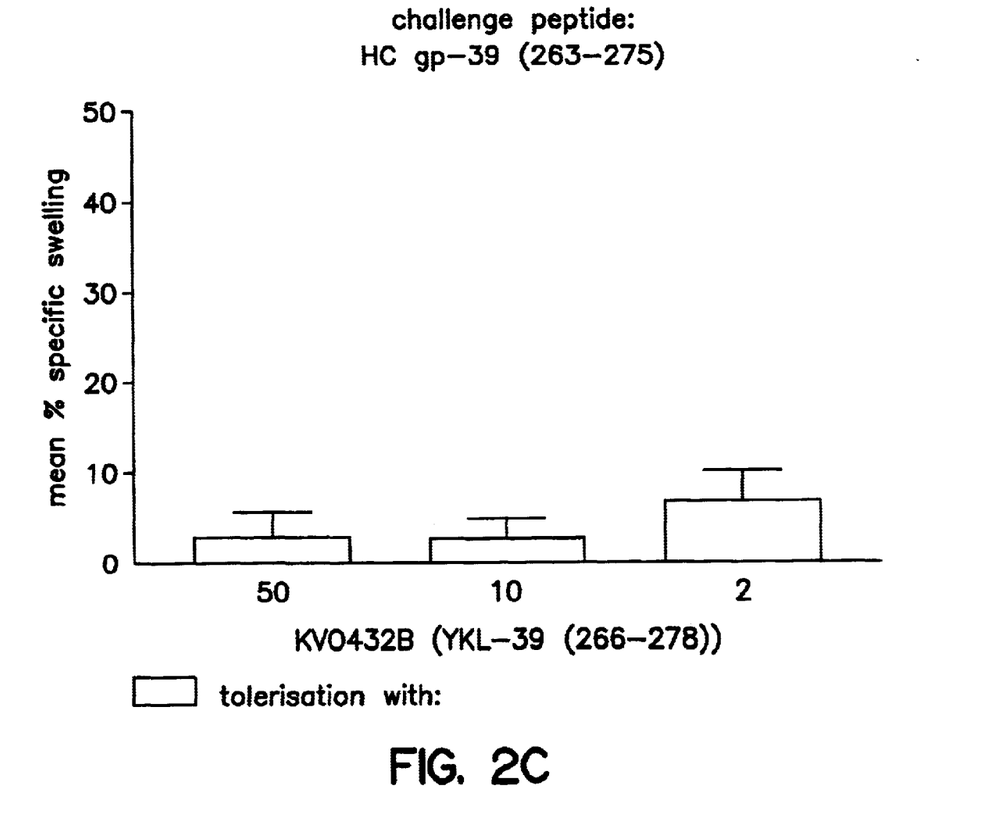

A HC gp-39 (263–275)-specific DTH assay suitable to monitor tolerance induction with peptide antigens was developed. Immunisation of Balb/c mice with HC gp-39 (263–275) in incomplete Freunds adjuvant (IFA) was found to be effective in the induction of a DTH response following challenge with the HC gp-39 (263–275) peptide. This peptide-based DTH system was used to detect modulation of the DTH response by nasal application of HC gp-39 (263–275) peptide. It was found that nasal application of HC gp-39 (263–275), in a dose-dependent manner, downmodulated the HC gp-39 (263–275) induced DTH response. Nasal application of YKL-39 (266–278), however, resulted in a more enhanced downmodulation of the DTH response, indicating that YKL-39 (266–278) can efficiently tolerize a peptide-specific response induced with HC gp-39 (263–275) (Table 4, FIG. 2a,b,c).

TABLE 4

Experimental set-up tolerization experiment

| Pretreatment | sensibilisation | challenge | tolerance |
|---|---|---|---|
| none | HC gp-39 (263-275) | HC gp-39 (263-275) | no |
| saline | HC gp-39 (263-275) | HC gp-39 (263-275) | no |
| HC gp-39 (263-275) | HC gp-39 (263-275) | HC gp-39 (263-275) | yes |
| YKL-39 (266-278) | HC gp-39 (263-275) | HC gp-39 (263-275) | yes |

---

What is claimed is:

1. An isolated peptide of 9–55 amino acids comprising the amino acid sequence FTLASAETT (SEQ ID NO: 1).

2. An isolated peptide of 13–55 amino acids comprising the amino acid sequence HSFTLASAETTVG (SEQ ID NO: 2).

3. The peptide according to claim 1 having an amino acid sequence of 9 to 25 amino acids.

4. The peptide according to claim 1 consisting essentially of the amino acid sequence FTLASAETT (SEQ ID NO: 1) or HSFTLASAETTVG (SEQ ID NO: 2).

5. Pharmaceutical composition comprising at least one peptide according to claim 1 and a pharmaceutically acceptable carrier.

6. A method for the manufacture of a pharmaceutical preparation for the induction of specific T-cell tolerance to an autoantigen in patients suffering from autoimmune disorders, comprising combining a peptide according to claim 1 with a pharmaceutically acceptable carrier.

7. Diagnostic composition comprising at least one peptide according to claim 1 and a detection agent.

8. The peptide according to claim 2 having an amino acid sequence of 13 to 25 amino acids.

9. A method for detecting autoreactive T-cells comprising: providing peripheral blood mononuclear cells, culturing the peripheral blood mononuclear cells; incubating the peripheral blood mononuclear cells with at least one peptide according to claim 1; and detecting a reeponse of the peripheral blood mononuclear cells to the presence of the peptide.

\* \* \* \* \*